United States Patent
Dacremont

(10) Patent No.: US 9,877,807 B2
(45) Date of Patent: Jan. 30, 2018

(54) ADDITIONAL STABILIZATION DEVICE FOR ENDO-OSSEOUS DENTAL IMPLANT

(75) Inventor: Philippe Dacremont, Sanary sur Mer (FR)

(73) Assignee: SADDLE IMPLANT TECHNOLOGIES SARL, Geneva (CH)

(*) Notice: Subject to any disclaimer, the term of this patent is extended or adjusted under 35 U.S.C. 154(b) by 295 days.

(21) Appl. No.: 12/865,810

(22) PCT Filed: Jul. 20, 2010

(86) PCT No.: PCT/FR2010/051529
§ 371 (c)(1),
(2), (4) Date: Aug. 2, 2010

(87) PCT Pub. No.: WO2011/010061
PCT Pub. Date: Jan. 27, 2011

(65) Prior Publication Data
US 2011/0171601 A1    Jul. 14, 2011

(30) Foreign Application Priority Data
Jul. 22, 2009   (FR) ..................................... 09 55129

(51) Int. Cl.
*A61C 8/00* (2006.01)

(52) U.S. Cl.
CPC .......... *A61C 8/0009* (2013.01); *A61C 8/0031* (2013.01)

(58) Field of Classification Search
CPC ............................ A61C 8/0031; A61C 8/0009
USPC ... 433/18, 172–176, 201.1, 202.1, 215, 220, 433/221; 606/280–299, 70–71
See application file for complete search history.

(56) References Cited

U.S. PATENT DOCUMENTS

| | | | |
|---|---|---|---|
| 5,052,930 A * | 10/1991 | Lodde et al. | 433/173 |
| 5,116,225 A * | 5/1992 | Riera | 433/173 |
| 5,362,235 A * | 11/1994 | Daftary | 433/172 |
| 5,513,989 A | 5/1996 | Crisio | |
| 5,944,526 A * | 8/1999 | Liu | 433/176 |
| 6,250,922 B1 * | 6/2001 | Bassett et al. | 433/172 |
| 2002/0150856 A1 * | 10/2002 | Payton | 433/8 |
| 2003/0194679 A1 * | 10/2003 | Odrich et al. | 433/173 |
| 2003/0235805 A1 * | 12/2003 | Lax | 433/220 |
| 2006/0154205 A1 * | 7/2006 | Reggie | 433/173 |

FOREIGN PATENT DOCUMENTS

| | | |
|---|---|---|
| DE | 199 36 061 | 3/2000 |
| FR | 2 915 677 | 11/2008 |
| WO | 2001/93775 | 12/2001 |

* cited by examiner

*Primary Examiner* — Heidi M Eide
(74) *Attorney, Agent, or Firm* — Lucas & Mercanti, LLP

(57) ABSTRACT

A stabilization device intended to be used in addition and in combination with an endo-osseous dental implant, the endo-osseous implant having at least one endo-osseous anchoring foot adapted to an installation in a jaw bone of a patient so as to cooperate with an external pillar intended to be fixed into the anchoring foot and further fixing a dental prosthetic element, and the relative movements of the pillar relatively to the anchoring foot may be anti-rotationally inhibited, once the pillar is placed in the anchoring foot.

2 Claims, 4 Drawing Sheets

ADDITIONAL STABILIZATION DEVICE FOR ENDO-OSSEOUS DENTAL IMPLANT

This is a National phase of PCT/FR2010/051529 filed Jul. 20, 2010, which claims the priority of FR 09 55129 filed Jul. 22, 2009, both applications are incorporated by reference herein.

BACKGROUND OF THE INVENTION

The present invention relates to the general field of dental implants.

More particularly, the invention relates to endo-osseous dental implants and more specifically to the stabilization of these implants.

Presently, endo-osseous implants are conventionally based on the use of an anchoring foot, for example an anchoring screw, adapted so as to be installed in a jaw bone of a patient. This anchoring foot cooperates with an external pillar intended to be fixed in the anchoring foot. The external pillar therefore comprises means for being fixed in the anchoring foot and means for fixing a dental prosthetic element which will cap the external pillar and protrude above the jaw bone of the patient in order to replace the missing dental element. The prosthetic outer pillar is stabilized relatively to the anchoring foot with anti-rotational means with which relative movements of the pillar relatively to this anchoring foot are inhibited.

Further, it is necessary to ensure primary stability of the implant in the bone by ensuring stability of the anchoring foot in the bone. This fact is determining for osteo-integration of the implant. Indeed, masticatory movements of the patient are as many agents for destabilizing this assembly by torsion, rotation, compression, etc., which the implant should be able to withstand.

Thus, two distinct cases occur in the treatment after laying down the anchoring foot.

In the first case, the bone is particularly dense and in a large amount, which unfortunately is rare, and it is then possible to immediately place the prosthetic pillar which is attached on the anchoring foot and to adhesively bond the dental crown on the latter.

In the second case, the anchoring foot is placed <<to be nursed>> during a healing period. This means that the anchoring foot is placed in the bone and the gums are closed over it. In this case, no force is applied and there are no risks of mobilization of the anchoring foot during the healing phase. Thus, a period of six months for a maxillary implant and three months for a mandibular implant is required for allowing healing. During this period, any mobilization or overload of the bone causes rejection of the anchoring foot. After this healing period, the gums are opened and the prosthetic pillar is set into place as well as the tooth.

Therefore, except in cases when the bone has very favorable density and amount, it is not possible to make the tooth during this period of time between three and six months.

Further, with this method, the results obtained on the bone level do not always allow proper stabilization of the implant. This is the case in particular if one is in presence of low density spongy bone, a bone of type 5 for example.

Then, as the primary retention of the implant is a primordial condition for its success, the anchoring foot cannot be left in the mouth and is therefore removed.

Presently, various means are therefore used for stabilizing the anchoring foot of the implant in the second case when bone is not present in a large amount. In particular, increasing the interface between the implant and the bone is sometimes contemplated, for example by a double thread at the surface of the implant or by using nanotechnologies for promoting the formation of a reliable bone interface between the bone of the jaw and the implant by remineralization of the tissues.

It is further noted that it is possible to finally use an exo-osseous implant which will bear upon the sidewalls of the gum while straddling them, in the cases when the bone is very degraded. Such an exo-osseous implant may also comprise an element with an anchor shape. In this case, the implant comprising a plate, a pillar and an anchoring element is designed so as to be installed as an assembly. Typically, the pillar and the anchoring element each interact differently with the plate which will straddle the gum. Anti-rotational means are sometimes borne by the plate and the pillar in order to avoid pivoting of the pillar. This is for example the case in the device described in patent application WO 01/93775.

In known devices, there is no intention of providing the anchoring foot with anti-rotational means. Indeed, it is noted that this is then unnecessary since no movement is able to occur between the plate and the anchoring foot. This solution nevertheless has the disadvantage of having to systematically install the plate/foot/pillar assembly and of not being able to modulate this installation.

In spite of the development of implant technology, it happens that endo-osseous implants continue to have mobility at the end of the healing period and are therefore subject to a lack of osteo-integration.

In view of the foregoing, it is actually seen that there exists a need for improving the stabilization of endo-osseous implants relatively to the jaw bone. Further, if it is possible to increase primary retention of the implant as soon as it is installed, it would be possible, in the majority of the cases, to no longer wait for the end of the healing phase in order to make the prosthetic portion.

OBJECT AND SUMMARY OF THE INVENTION

The present invention therefore has the main object of proposing an additional stabilization device intended to operate in combination with an endo-osseous dental implant.

The invention for this proposes an additional stabilization device intended to be used in combination with an endo-osseous dental implant, such an endo-osseous implant comprising at least one endo-osseous anchoring foot adapted to installation in a jaw bone of a patient so as to cooperate with an external pillar intended to be fixed in the anchoring foot and further comprising means for fixing a dental prosthetic element, the anchoring foot and the pillar further comprising anti-rotational means with which the relative movements of the pillar relatively to the anchoring foot may be inhibited once the pillar is placed in the anchoring foot with or without installation of the additional device, the additional stabilization device being characterized in that it comprises a substantially rigid central platform perforated at its centre so as to allow introduction of the pillar into the anchoring foot of the implant through the stabilization device, the perforation of the platform being of a shape such that it cooperates with the anti-rotational means of the pillar and of the anchoring foot in order to inhibit rotational movements of the pillar in addition to the anti-rotational means of the pillar and of the anchoring foot, the device also comprising at least on either side of the central platform, two flexible side slender anchoring extensions so as to be able to be placed straddling the bone of the jaw, flattened onto either side of the latter, each extension comprising at least one orifice for positioning at least one fixing screw.

With such an additional device, by using anti-rotational means of the endo-osseous dental implant itself implemented on the anchoring foot and on the pillar on the one hand and, the sidewalls of the bones of the jaw on the other hand. As these walls are in very high density cortical bone unlike cancellous bone, increased stabilization of the endo-osseous implant is obtained.

The additional stabilization device according to the invention is, during its installation in the mouth, crossed by the base of the external pillar which will be housed in the anchoring foot. This is therefore a device which is totally independent of the actual endo-osseous implant, which allows it to be either installed or not, optionally, depending on the conditions encountered by the implantologist.

Insofar that the anchoring foot and the pillar themselves comprise anti-rotational means, it is not absolutely necessary to install the additional device according to the invention. In fact, the principle governing the structure and operation of the additional device according to the invention is actually the fact of it being an optional installation. For this, the device according to the invention has a specific perforation able to cooperate with the own anti-rotational means of the pillar and of the anchoring foot, always present on the latter and which may operate alone in the absence of the additional device.

It is noted here that the additional stabilization device according to the invention may be permanently used in the mouth of the patient in order to permanently stabilize the endo-osseous implant. In particular, the use of the stabilization device according to the invention by increasing the primary stability as soon as it is installed may give the possibility of omitting the phase for awaiting healing before placing the dental prosthesis. The healing phase therefore occurs after installing the pillar and the dental prosthesis. The stabilization device according to the invention then ensures sufficient stability to the implant so that it is not necessary to carry out intermediate steps, notably waiting steps.

The implant may then be completely installed during a single and same intervention in more numerous cases than presently. Indeed, even in the cases when the bone of the jaw is not very favorable at the installation of the implant, the installation of a stabilization device according to the invention, it is possible to carry out this installation in one go, which is not the case presently. This is very advantageous for the patient. Generally the stabilization device is then left permanently.

In less favorable cases, it is also contemplated that the stabilization device may be used for complementary stabilization during a nursing phase during which the prosthetic pillar is typically not installed. In this case, instead and in place of the prosthetic pillar, a very short covering screw of same connection technology as the pillar is used for plugging the orifice of the anchoring foot intended to receive the pillar subsequently and for firmly attaching the stabilization device according to the invention with the anchoring foot. With this it is possible to replace the gum over it and wait. Then, at the moment of the installation of the pillar and of the dental prosthesis, the stabilization device may be left permanently or be removed before placing the prosthetic pillar. This functionality is not known in known devices.

The device according to the invention may therefore also be only used temporarily during the healing period of the endo-osseous implant while also optionally allowing the making of a temporary prosthetic element during this period.

It was seen that this period corresponds to the progression of the remineralization and bone reconstitution process. To summarize, at the end of this process, the stabilization device may, optionally and depending on the needs, be removed or left in place in order to strengthen the stability of the implant in a permanent way. Whatever the case, the invention allows installation of the same provided pillar whether the additional device has to be left in place or not. This avoids having to multiply the provisions and manage the supplies.

In the case when it is removed, the device according to the invention is then used punctually and removed from the mouth of the patient from the moment when remineralization is sufficient for stabilizing the anchoring foot. The installation of the pillar provided on the anchoring foot then only uses the own anti-rotational means of both of these elements without it being necessary to modify the pillar or other elements.

It is noted here that the stabilization device according to the invention may, if need be, be easily installed and deinstalled from the mouth of the patient after removal of the prosthetic element and of the prosthetic pillar or after removing a screw of same connection technology and shorter in the case of "nursing".

According to a preferential characteristic of the invention, at least one of the side extensions is formed by a Y-shaped arm, each branch of the Y being provided with an orifice for positioning a fixing screw.

This characteristic is particularly important for maintaining the additional stabilization device in position. Indeed, the Y shape of at least one of the side extensions of the device allows it to follow the lines of stresses generated by the rotational and torsional movements related to mastication of the patient. Also, such a shape of the side extensions provides strong limitations of the stresses detrimental for the integrity of the stabilization device. Strong stresses on the thin arms forming the slender extensions of the device according to the invention may indeed cause breakage of the side extensions.

Very advantageously in order to ensure good stabilization of the implant, both orifices of the branches of a same Y are separated by at least the width of the endo-osseous implant.

According to another possible feature of the invention, at least one of the side extensions is formed by a T-shaped arm, each branch of the T being provided with an orifice for positioning a fixing screw.

This configuration of the device less favorable from the point of view of the distribution of the stresses on the stabilization device may however be contemplated according to the invention. The stresses generated by the mastication of the patient may in this case generate breakage of one of the arms of the T more easily than in the case when a Y-shaped side extension is used.

Here also, advantageously, as both orifices of the branches of a same Y are separated by at least the width of the endo-osseous implant. Advantageously both side extensions are formed by Y-shaped or T-shaped arms, each branch of the Y or of the T being provided with an orifice for positioning a fixing screw. With this feature it is possible to optimize the fixing of the additional stabilization device in the mouth of the patient. In this case, by using Y side extensions on either side of the same platform, the stresses generated in torsion by mastication are allowed to be mainly exerted on two opposite branches of the Ys on either side of the central platform.

In a first embodiment, as the device is intended to be installed in combination with an endo-osseous implant having anti-rotational means so that the anchoring foot and the pillar respectively comprise female and male portions with matching regular polygonal shapes, the stabilization device is then such that the perforation of the platform has a regular polygonal shape, allowing inhibition of the relative movement of the male portion of the pillar and of the stabilization device by contact of the surfaces of the polygonal male portion of the pillar with the polygonal surfaces of the perforation of the platform.

With these particular features, the relative movements of the different elements forming the endo-osseous implant and the stabilization device are not allowed to occur. Such movements, if they were possible, would of course be detrimental to the stabilization of the dental implant by the additional stabilization device.

One of the advantages of this embodiment is to ensure, by mechanical pressure of both surfaces in abutment on each other, inhibition of the relative movements between the male portion of the pillar and the additional stabilization device. This abutment pressure allows the anti-rotational function to be ensured even in the presence of slight unscrewing of the screw which maintains the external pillar firmly attached to the anchoring foot.

In a particular embodiment, the regular polygonal shape of the perforation of the platform is the same as that of the male and female portions of the anchoring foot and of the pillar.

This embodiment ensures very efficient immobilization of the male portion of the pillar, relatively to the stabilization device since the totality of the surfaces are in contact. On the other hand, the stabilization device should be installed while observing one of the angular orientations of the polygon as oriented by the position of the anchoring foot in the bone of the jaw.

According to a more flexible embodiment, the regular polygonal shape of the perforation of the platform allows more positions of the stabilization device than a regular polygonal shape identical with that of the pillar.

With this functional feature, it is possible to adjust the position of the stabilization device relatively to the male portion of the pillar, with greater accuracy than the minimum angular movement amplitude authorized by the regular polygonal shape of the pillar and of the anchoring foot.

In a particular embodiment, as the polygonal shapes of the pillar and of the anchoring foot have n sides, the perforation of the stabilization device has a polygonal shape with 2n sides.

This embodiment allows shifting of the pillar and stabilization device by half the minimum angle authorized by the regular polygonal shape implemented in the anti-rotational means of the pillar and of the anchoring foot.

Thus, in particular embodiments, as the polygonal shapes of the pillar and of the anchoring foot are hexagonal, the perforation of the stabilization device has a dodecagonal shape, i.e. twelve sides. This embodiment is preferential since it allows orientation of the stabilization device relatively to the external pillar and to the anchoring foot with angles of 30°, which proves to be sufficient for positioning the stabilization device in the mouth.

In another less advantageous embodiment than the previous one, as the polygonal shapes of the pillar and of the anchoring foot are square, the perforation of the stabilization device has an octagonal shape.

This embodiment, allowing orientation of the external pillar with the stabilization device every 45°, allows a rather small adaptation of the relative positionings of both of these elements but nevertheless it may be achieved according to the invention.

In another embodiment, as the stabilization device is intended to be installed in combination with an endo-osseous dental implant having frictional anti-rotational means, the stabilization device is such that the size of the perforation and the shape of the surface surrounding the perforation in the platform are such that it allows the anti-rotational frictional surfaces of the pillar and of the anchoring foot to be in frictional contact with the central platform of the stabilization device.

With this embodiment, it is possible to perforate the stabilization device through a simple circular hole, allowing the passage of the base of the external pillar towards the anchoring foot. In this embodiment, the anti-rotational frictional surfaces of the anchoring foot and of the external pillar are no longer in contact with each other but each of them is in contact with one of the faces of the stabilization device according to the invention.

According to an application, as the anti-rotational frictional means are such that the anchoring foot and the pillar respectively comprise matching female and male conical shapes, the stabilization device is such that the central platform is embossed as a cone around the central perforation.

With such an embodiment, the frictional surface of the additional stabilization device is allowed to match the shape of the surfaces of the pillar and of the anchoring foot intended to be in frictional contact with each other in order to prevent relative rotations of both of these elements.

According to a particular feature of the invention, one of the side extensions is longer than the other one and is then intended to be fixed on the vestibular side of the jaw.

This feature allows differentiation of the vestibular side and of the palatine side and allows better adaptation of the additional stabilization device in the mouth of the patient.

Advantageously, the thickness of the stabilization device is comprised between 0.2 and 1 mm and preferably between 0.4 and 0.8 mm.

According to advantageous feature, the length of the stabilization device is comprised between 6 and 25 mm and preferably between 7 and 16 mm.

More specifically, according to advantageous features of the invention, the lengths of the side extensions are comprised between 3 and 6 mm on the palatine side and between 4 and 10 mm on the vestibular side.

The dimensional features above allow proper installation of the stabilization device according to the invention and adaptation of the device according to the size of the jaw of the patient and to the bones of the jaw.

The invention also relates to a dental implantation kit comprising an endo-osseous dental implant and a stabilization device according to the invention and at least two osteo-integrable screws for adjusting and fixing the stabilization device on a maxillary or mandibular jaw bone.

SHORT DESCRIPTION OF THE DRAWINGS

Other features and advantages of the present invention will become apparent from the description made below with reference to the appended drawings which illustrate an exemplary embodiment thereof without any limitation:

FIGS. 1A and 1B respectively show an exploded perspective view of an endo-osseous implant during its installation in combination with an additional stabilization device according to the invention and a perspective view of an implant installed with an additional stabilization device according to the invention;

Figure 4A:
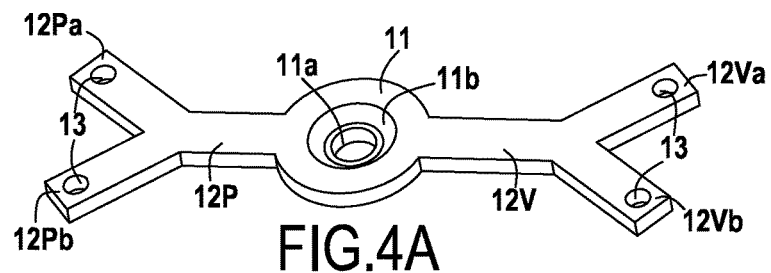
Figure 4B:
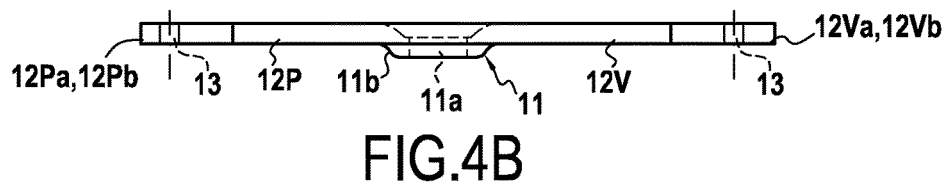
Figure 5:
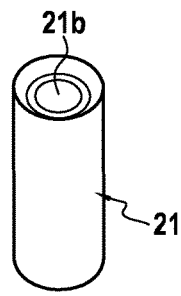
Figure 6:
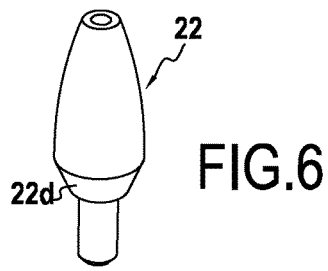
Figure 7:
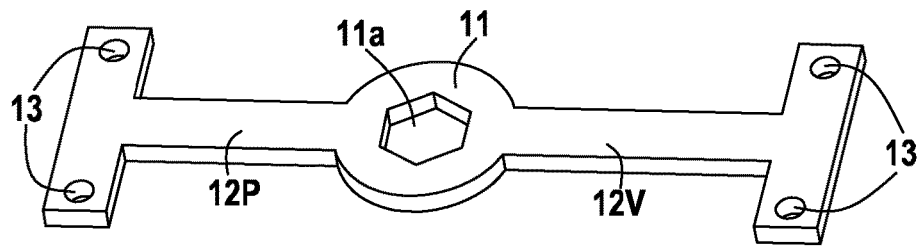
Figure 8:
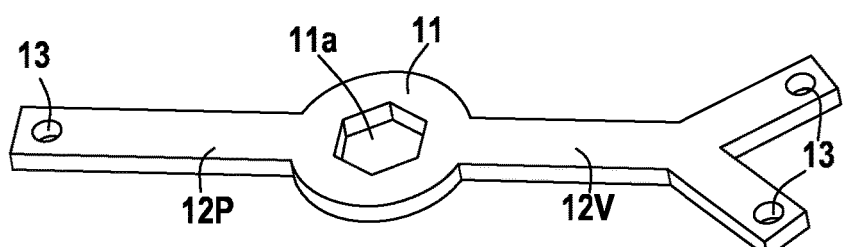
Figure 9:
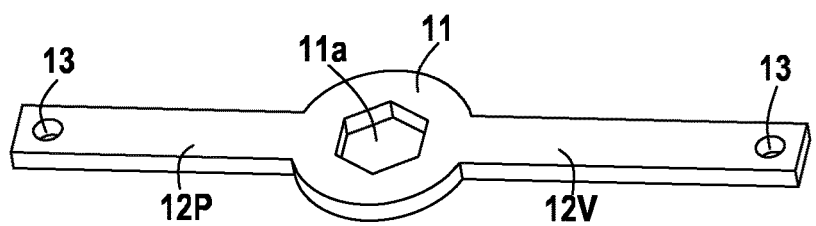
Figure 10:
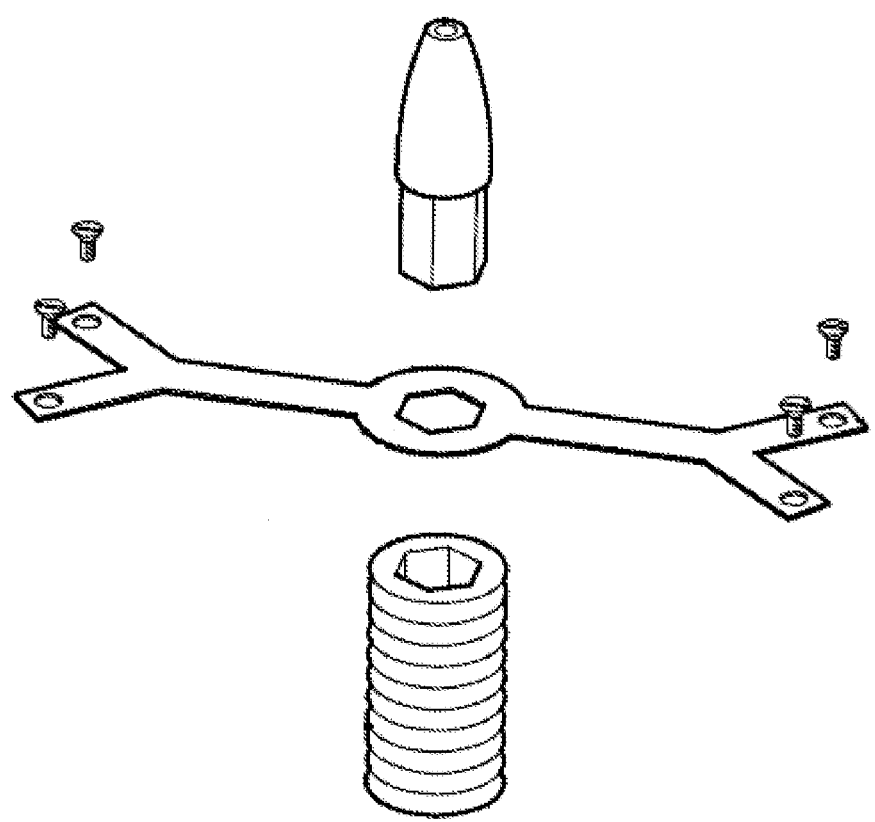

FIGS. 4A and 4B respectively show a top view and a side view of a stabilization device according to an application of a second embodiment according to the invention;

FIG. 5 schematically shows an anchoring foot capable of cooperating with the stabilization device illustrated in FIG. 4;

FIG. 6 schematically shows an external pillar capable of cooperating with the stabilization device illustrated in FIG. 4;

FIG. 7 shows a possible embodiment of a stabilization device according to the invention;

FIG. 8 shows another possible embodiment of a stabilization device according to the invention;

FIG. 9 further shows another possible embodiment according to the invention; and FIG. 10 shows a dental implant kit of the endo-osseous implant with an additional stabilizer device according to the invention.

DETAILED DESCRIPTION OF AN EMBODIMENT

Figure 1A:
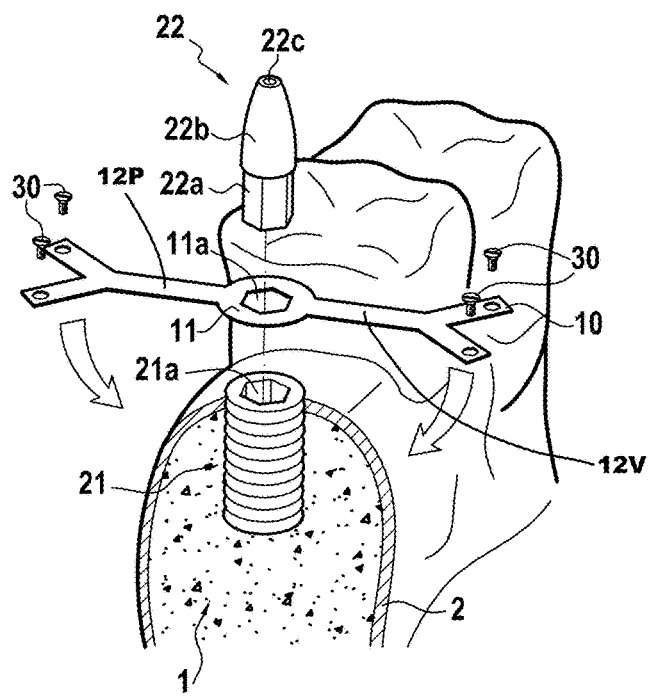

FIG. 1A schematically illustrates a jaw bone 1 covered with gingival tissue 2. This bone 1 was perforated so as to introduce an anchoring foot 21 of an endo-osseous dental implant, comprising this anchoring foot 21 and an external pillar 22. The pillar 22 comprises a base 22*a* which forms a male portion matching a female portion 21*a* which is an orifice 21*a* made in the anchoring foot 21. These matching portions give the possibility of achieving a mechanical link by introducing the base 22*a* into the orifice 21*a*.

The external pillar 22 further comprises a nipple 22*b*, on which the prosthetic element is intended to be placed. The pillar 22 comprises a central bore 22*c* perforating it over the whole of its length and being aligned with another central bore made at the bottom of the orifice 21*a* in the anchoring foot 21 when the pillar 22 is engaged into the anchoring foot 21. These bores are intended to receive a locking screw fixing the pillar 22 to the anchoring foot 21.

Such a structure of an endo-osseous implant is well-known. The male portions 22*a* of the external pillar and the female portions 21*a* of the anchoring foot bear anti-rotational means with which the movements of the external pillar 22 relatively to the anchoring foot 21 are inhibited.

In FIG. 1A, it is seen that the anti-rotational means are based on the use of the male and female portions with hexagonal matching sections, i.e. as a regular six-sided polygon. It is actually seen here that the pillar and the anchoring foot bear their own anti-rotational means allowing them to be immobilized relatively to each other, whether an additional device is installed or not.

In this figure, such an optional additional stabilization device 10 according to the invention is also illustrated. This additional stabilization device 10 comprises a substantially rigid central platform 11, perforated in its centre 11*a* so as to allow introduction of the base of the pillar 22*a* into the anchoring foot 21 of the implant through the stabilization device 10.

According to the invention, it is seen in this figure that the perforation 11*a* of the platform 11 is of such a shape that it cooperates with the anti-rotational means of the pillar 22 and of the anchoring foot 21. Indeed, the perforation 11*a* has the same geometrical hexagonal shape as the sections of the male and female portions, of the pillar 22 and of the anchoring foot 21 respectively. Thus, when the base 22*a* of the pillar 22 is introduced into the orifice 21*a* of the anchoring foot 21 through the stabilization device 10, the stabilization device 10 which is intended to be fixed to the bone of the jaw by screws 30, still further inhibits the rotational movements of the pillar 22 in addition to the anti-rotational means between the pillar 22 and the anchoring foot 21.

Indeed, it is made interdependent in rotation with the anchoring foot and the pillar by the presence of the central hexagonal shape which makes it cooperate with the own anti-rotational means of the pillar and of the anchoring foot. The independence of the own anti-rotation means of the anchoring foot and of the pillar is well understood, either with the installation or not of the additional device. It is also well understood that the specific shape of the perforation is specifically adapted to the own independent anti-rotational means of the pillar and of the anchoring foot. It is also noted that the installation of the plate which forms the additional device, can by no means be accomplished in the absence of either one of the two elements, the pillar and the anchoring foot, or in the absence of anti-rotational means of the pillar and of the anchoring foot.

In order to be immobilized relatively to the bone of the jaw, the stabilization device 10 comprises two Y-shaped flexible anchoring side extensions 12P and 12V. Each of the branches of the Y has an orifice noted as 13, allowing placement of an osteo-integrable screw 30.

Advantageously, the distance between the orifices 13 in order to receive the side screws allowing the stabilization device to be maintained, will depend on the size of the endo-osseous implant. It is thus noted that advantageously, both fixing screws are spaced apart by at least the width of the endo-osseous implant.

With this fixing to the bone of the jaw of an element moreover immobilized relatively to the implant, it is possible to block very efficiently the rotational movements which may be exerted on the endo-osseous implant.

Figure 1B:
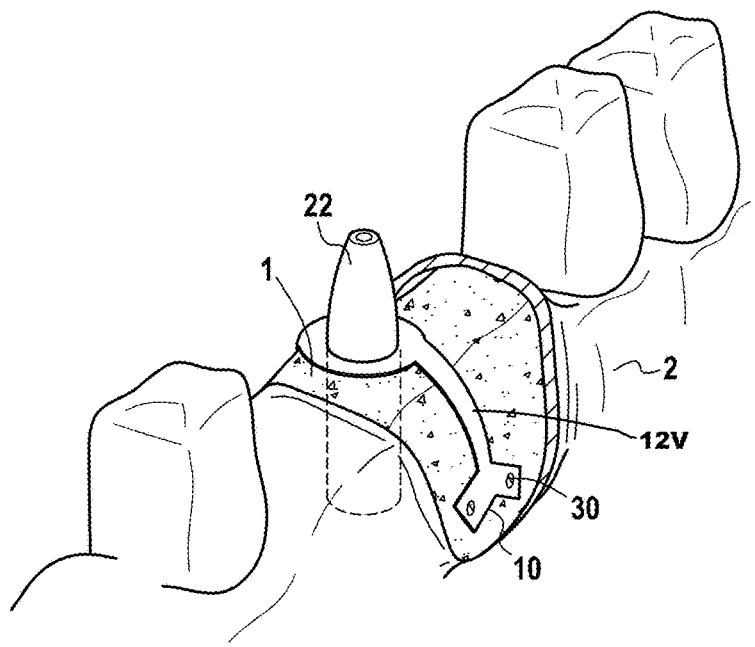

As this is illustrated in FIG. 1B, the side anchoring extensions 12P and 12V are such that they are intended to be placed straddling the bone of the jaw 1 under the gingival tissue 2, which is incised and lifted beforehand in order to place the stabilization device. The stabilization device according to the invention is advantageously made from a material treated by anodic oxidation.

Figure 2:
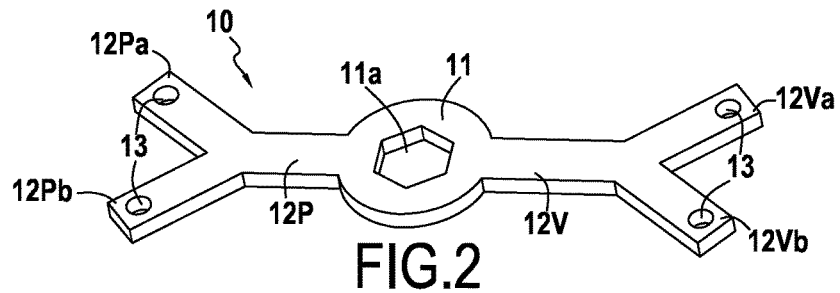
FIG. 2 show a stabilization device according to a first application of a first embodiment according to the invention.

FIG. 2 shows a first application of a first embodiment according to the invention, wherein the perforation 11*a* of the central platform 11 has a hexagonal shape. The central portion 11 has two side extensions as arms 12P and 12V which each assume the shape of a Y and therefore comprise at their ends, two branches, 12Va, 12Vb and 12Pa, 12Pb, respectively. It is noted in this figure that the arm 12V is longer than the arm 12P. This meets an anatomic need. Indeed, it is desirable that the side extension 12V intended to be fixed on the vestibular side be longer than the side extension 12P intended to be fixed on the palatine side.

Figure 3:
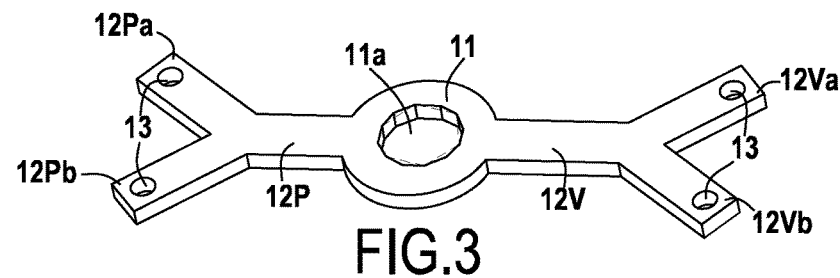
FIG. 3 shows a stabilization device according to a second application of a first embodiment according to the invention.

FIG. 3 illustrates a second application of the first embodiment according to the invention, wherein the perforation 11*a* comprises twelve sides and therefore has a dodecagonal regular polygon shape. This application gives the possibility of placing the hexagon of the pillar 22 illustrated in FIG. 1 inside the perforation 11*a* in six different angular positions relatively to the stabilization device instead of three with the first application of the first embodiment illustrated in FIG. 2.

This therefore allows better adjustment of the positioning of the stabilization device 10 relatively to both the jaw and the male and female portions of the external pillar 22 and of the anchoring foot 21. This allows more adaptable and therefore more efficient positioning of the stabilization device 10. Insofar that the hexagon, illustrated in dotted lines in FIG. 3, abuts anyway on the surface of the dodecagon of the stabilization device 10, the anti-rotational properties are ensured between the device and the anchoring foot/pillar assembly.

FIG. 4 shows a stabilization device according to an application of a second embodiment. This stabilization device 10 is intended to operate by cooperating with an implant comprising an anchoring foot of the type of the one illustrated in FIG. 5 and an external pillar of the type of the one illustrated in FIG. 6. In this embodiment, anti-rotational frictional means are used between the external foot 22 of FIG. 6 and the anchoring foot 21 of FIG. 5 in order to inhibit their relative movements. Such anti-rotational frictional means are generally formed by a portion 22d of the base of the pillar 22 having a conical shape and intended to bear upon a matching also conical shape 21b of the anchoring foot 21. When the external pillar 22 is placed in the anchoring foot and fixed by screwing a screw introduced into the orifice 22c, the presence of the conical surfaces rubbing against each other gives the possibility of avoiding relative rotation of the pillar 22 relatively to the anchoring foot 21. Here again, the independence of these anti-rotational means implemented on the anchoring foot and the pillar is understood relatively to the installation or not of an additional stabilization device according to the invention.

In FIG. 4, the stabilization device 10 thus comprises a perforation 11a surrounded by an embossed area 11b as a cone portion, similar to that of the frictional surfaces of the external pillar 22 and of the anchoring foot 21.

FIG. 5 illustrates an anchoring foot 21 comprising a surface as a conical portion 21b intended to come into contact with a male cone portion 22d, present on the external foot 22, as illustrated in FIG. 6.

The embossed area 11b around the perforation 11a of the complementary stabilization device illustrated in FIGS. 4A and 4B forms two identical surfaces, at the surface of the pillar and at the surface of the foot on either side of the stabilization device respectively. The lower face of the stabilization device is thus allowed to bear upon the frictional surface 21b of the anchoring foot 21. Further, when the external pillar 22 is introduced into the anchoring foot 21, the cone portion surface 22d of the pillar 22 comes into contact with the upper face of the embossed area 11b. This thereby blocks by friction all the relative movements of the three mechanical parts.

It is moreover noted that the surfaces of the pillar and of the anchoring foot have to be such that they may cooperate as frictional surfaces with or without the stabilization device.

FIGS. 7, 8 and 9 show possible particular embodiments of stabilization devices according to the invention.

In FIG. 7 the side extensions are T-shaped, each branch of the upper portion of the T being provided with an orifice allowing osteo-integrable fixing screws to be placed in the bone of the jaw.

It is understood that this possible embodiment of the invention has the drawback that the branches and arms of the side extensions do not follow the lines of stresses which the stabilization device according to the invention is likely to have to withstand. Thus, this embodiment, although allowing participation in the stabilization of the endo-osseous implant, has the disadvantage of the risk of having weaknesses, or even breakages, at the branches of the T.

FIG. 8 shows an embodiment according to which a side extension has a shape of a Y, while the other one is a simple straight arm provided at its end with an orifice 13 so that only one fixing screw is placed therein. Such a single straight arm is advantageously shifted relatively to the major axis of the stabilization device. This shift will for example be by an angle of less than or equal to 20° and preferably between 8 and 15°. Such a shift prevents the fixing screw of the stabilization device from being able to touch the anchoring foot during the fixing of the stabilization device. The selection of the value of this shift angle depends on the length of the single arm and in particular on this length relatively to the depth of the anchoring foot. This embodiment allows stabilization of the endo-osseous implant but with not so good performance as when four screws placed on the Y or T side extensions are used.

Indeed, it is understood that a simple arm only supporting one orifice for placing a fixing screw, will be more capable of bending under a stress than a device comprising Y arms for placing two screws distant by at least the width of the implant. Finally, FIG. 9 illustrates an embodiment of the stabilization device in which both side extensions are simple arms provided at their ends with an orifice 13 for introducing a fixing screw on the bone of the jaw.

It should be noted that such an embodiment does not allow much stabilization of the endo-osseous implant in torsion in spite of it properly participating in the additional stabilization of the implant in rotation.

It is noted that a stabilization device according to the invention may be installed with various types of conventional endo-osseous cylindrical implants existing beforehand from the moment that they have anti-rotational means. It is then well understood that the features of the perforation of the additional device are then adapted to these anti-rotational means of the implant to be installed.

As the invention allows greater stabilization of the endo-osseous implant, it avoids multiplication of the installation of implants, for example for installing a bridge, or further waiting for long months in order to achieve the installation of a prosthesis. In particular, for the installation of a bridge on three teeth, it will be possible to only place two implants instead of three as this is presently practiced.

Further it is noted that the Y or T shape of the side extensions of the stabilization device which are only formed on fine arms, allows a small portion of the bone to be covered. With this, it is possible not to compromise the remineralization and reconstitution mechanism of the bone tissue around the perforation made for placing the anchoring foot in the bone of the jaw. Elements covering the bone on wider areas prevent proper vascularization from being maintained which would be detrimental to proper bone reconstruction.

Finally, it is noted that various applications may be achieved according to the principles of the invention. In particular, the anti-rotational means may be accumulated, i.e. they may combine a polygonal shape with a conical frictional surface. For example the external pillar of FIG. 5 would then comprise a base of hexagonal section under the cone instead of a cylindrical base as illustrated. The foot would then comprise an orifice with a section which is also hexagonal under the conical surface.

Finally, it is noted that other further mixed embodiments may be achieved, using either one of the shapes of the side extensions and either one or both of the anti-rotational means presented in the description above.

The invention claimed is:

1. A stabilized dental implant device comprising:
   a stabilization device; and
   an endo-osseous dental implant configured to be used in combination with the stabilization device, the endo-osseous dental implant comprising:
   an independent and separate endo-osseous anchoring foot configured to be screwed in a jaw bone of a patient, the endo-osseous anchoring foot comprising a non-threaded conical cavity forming a female portion, and
   an independent and separate external pillar having a conical lower part and an upper part on which a dental prosthetic is fixable directly,
   the stabilization device comprising:
   a substantially rigid platform comprising a circular perforation surrounded by an embossed area, the circular perforation allowing the introduction of the conical lower part of the external pillar into the conical cavity of the anchoring foot through the stabilization device, so that the platform is intercalated between the upper part of the external pillar and the anchoring foot thereby immobilizing the stabilization device relative to the endo-osseous dental implant once the external pillar is fixed to the endo-osseous anchoring foot,
   wherein the conical cavity, the conical lower part, and the circular perforation cooperate such that once the conical lower part of the pillar has been has been non-rotatably introduced and fixed in the conical cavity of the anchoring foot through the circular perforation of the platform, the conical lower part contacts an upper face of the embossed area and blocks by friction all the relative movements of the pillar, the anchoring foot, and the platform, and
   two flexible anchoring side slender extensions, each of the slender extensions forming a Y-shape with a base portion having a first end at the circular perforation and extending to a second end connected to two branches of the Y-shape, each of the branches comprising an orifice for positioning an osteo-integrable fixing screw in the jaw bone to thereby fix the stabilization device and prevent rotation movement which may be exerted on the endo-osseous dental implant,
   the slender extensions extending on two opposite sides of the circular perforation so as to be able to be placed straddling the bone of the jaw, each flexible anchoring side slender extension being flattened on either side of the bone; and
   the endo-osseous dental implant being capable of being fixed independent of the stabilization device.

2. A stabilization device for cooperation with an independent and separate endo-osseous dental implant, the dental implant comprising an endo-osseous anchoring foot configured to be screwed in a jaw bone of a patient and comprising a non-threaded conical cavity and an independent and separate external pillar comprising a non-threaded conical lower part and an upper part on which a dental prosthetic is fixable directly, the stabilization device comprising:
   a substantially rigid platform comprising a circular perforation surrounded by an embossed area, the circular perforation allowing the introduction of the conical lower part of the external pillar into the cavity of the endo-osseous anchoring foot through the stabilization device, so that the platform can be intercalated between the upper part of the external pillar and the anchoring foot thereby immobilizing the stabilization device relative to the endo-osseous dental implant once the external pillar is fixed to the endo-osseous anchoring foot,
   the circular perforation and the conical lower part of the external pillar, introduced through the perforation of the platform, cooperating in order to further inhibit the rotational movements of the external pillar in addition to anti-rotational means of the external pillar and of the endo-osseous anchoring foot; and
   two flexible anchoring side slender extensions, each extension being formed by a Y-shaped arm, with a straight portion extending from the circular perforation and ending in two branches, each branch comprising an orifice for positioning an osteo-integrable fixing screw in the jaw bone, thereby fixing the immobilized stabilization device and blocking the rotation movement which may be exerted on the endo-osseous dental implant held thereby,
   the slender extensions extending on opposite sides of the circular perforation so as to be able to be placed straddling the bone of the jaw, each flexible anchoring side slender extension being flattened on either side of the bone.

* * * * *